United States Patent [19]

Terada et al.

[11] Patent Number: 4,673,761
[45] Date of Patent: Jun. 16, 1987

[54] PROCESS FOR PREPARING ANTI-INFLAMMATORY CYCLOALKYLIDENEMETHYLPHENYLACETIC ACID DERIVATIVES

[75] Inventors: Atsusuke Terada; Kazuyuki Wachi, both of Tokyo, Japan

[73] Assignee: Sankyo Company, Limited, Tokyo, Japan

[21] Appl. No.: 750,481

[22] Filed: Jun. 28, 1985

[30] Foreign Application Priority Data

Jul. 10, 1984 [JP] Japan ................................. 59-142567

[51] Int. Cl.$^4$ ............................................. C07C 59/86
[52] U.S. Cl. ..................................... 562/459; 560/051; 260/501.1; 260/501.11
[58] Field of Search .......................... 562/459; 560/051

[56] References Cited

U.S. PATENT DOCUMENTS 4,254,274 3/1981 Terader et al. ..................... 562/459

Primary Examiner—Paul J. Killos
Attorney, Agent, or Firm—Frishauf, Holtz, Goodman & Woodward

[57] ABSTRACT

Cycloalkylidenemethylphenylacetic acid derivatives of formula (I):

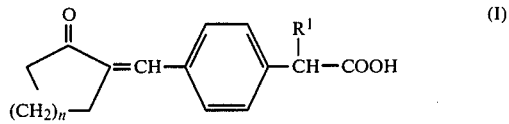

(wherein $R^1$ represents hydrogen or alkyl and n is an integer from 1 to 3) are prepared by reacting a benzaldehyde acid compound of formula (II):

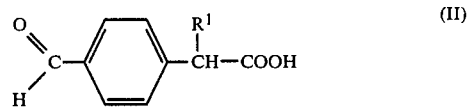

with an enamine derivative of formula (III):

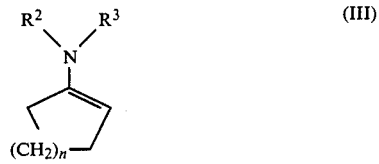

(wherein $R^2$ and $R^3$ are various organic groups) and then hydrolizing the product. The use of the acid of formula (II) rather than its corresponding ester enables the reaction to be effected with a good yield and under moderate and economical reaction conditions.

45 Claims, No Drawings

PROCESS FOR PREPARING ANTI-INFLAMMATORY CYCLOALKYLIDENEMETHYLPHENYLACETIC ACID DERIVATIVES

BACKGROUND OF THE INVENTION

The present invention relates to a new process for preparing certain known cycloalkylidenemethylphenylacetic acid derivatives which have valuable anti-inflammatory activities.

The cycloalkylidenemethylphenylacetic acid derivatives to which the present invention relates are described and claimed, inter alia, in U.S. Pat. No. 4,254,274 and may be represented by the formula (I):

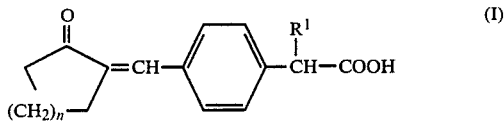

in which $R^1$ represents a hydrogen atom or a $C_1-C_4$ alkyl group and n is 1, 2 or 3. The preparation of such compounds is described and claimed in U.S. Pat. No. 4,365,076.

In the prior patent, the compounds are prepared by reacting a benzaldehyde carboxylic acid ester of formula (IIa):

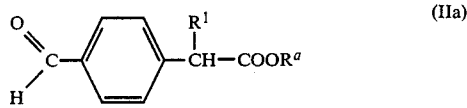

(in which $R^1$ is as defined above and $R^a$ represents a $C_1-C_3$ alkyl group) with an enamine derivative of formula (III):

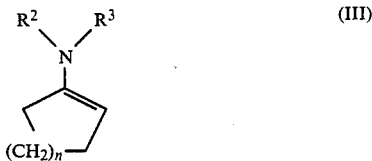

(in which n is as defined above and $R^2$ and $R^3$ are the same or different and each represents a $C_1-C_6$ alkyl group or they jointly form, together with the nitrogen atom to which they are attached, a cyclic amino group optionally having a ring oxygen atom). The product of the reaction of compounds (IIa) and (III), an intermediate which is not normally isolated, is then hydrolized to give an ester of the compound of formula (I); this ester may then be hydrolized to convert it to the acid, either as a separate step or, by carrying out the reaction between the compounds (IIa) and (III) in the presence of a suitable base, as part of the same step as that reaction.

Although this prior process works well, it is not totally satisfactory and there are certain elements involved in the process which could be improved in order to give a process which functions even more effectively on a commercial scale. Specifically:

(a) Thus, the aldehyde ester of formula (IIa) is normally prepared as a mixture comprising a major proportion of the desired para isomer and a minor proportion of the undesired ortho and meta isomers, these isomers all being oily compounds. As a result, a specific extra purification step is required to separate this mixture and obtain just the desired para isomer. It is possible to use the mixture of isomers of the esters (IIa) in the above reaction, to produce a mixture comprising the compound of formula (I) and the corresponding meta and ortho isomers, but these isomers still must be separated, which requires a specific purification step as they are all crystalline compounds.

(b) In the prior process, the most satisfactory solvents to use (from the point of view of ensuring a smooth reaction) are aromatic hydrocarbons, in particular benzene, which was successfully used in Examples 1 and 2 of U.S. Pat. No. 4,254,274 and No. 4,365,076. Benzene, however, is not the most desirable of solvents for use on an industrial scale as it pollutes the environment and has a deleterious effect on workers' health. Accordingly, when benzene is used on an industrial scale, measures are normally taken to protect the environment and the workers: these have an effect on the economy of the process. Other solvents which can be used are toluene and xylene; however, where these are used, in practice it is necessary to carry out the reaction at reflux temperature, and, even then, the reaction takes a long time. This adversely affects the economy of the process. None of these problems is unsuperable and, indeed, other factors may make it desirable to employ a solvent despite disadvantages of the type described above. However, it would clearly be desirable to provide a process for preparing compounds of formula (I) which can be operated more successfully in a wider range of solvents so as to provide the facility, if desired, of using a solvent free from these disadvantages or possessing them to a lesser degree.

(c) The final step of the above process comprises hydrolizing the ester to give the free-acid of formula (I). However, under the conditions required for this hydrolysis, cleavage of the enone carbon-carbon bond tends to occur, because of a retro-aldol reaction, which not only reduces substantially the yield of the desired product, but also increases the difficulty of purification of that product.

(d) As noted above, the final product will normally contain some of its ortho and meta isomers and will require purification to remove these. It would be desirable to provide a process which does not produce a final product containing these isomers and where, hence, purification can be simplified. For example, the most effective means of purifying the products of the prior process is by means of high vacuum distillation. It is an important and unexpected advantage of the present invention that simpler purification procedures can be used, if desired.

In conclusion, the prior process of U.S. Pat. No. 4,254,274 and No. 4,365,076 has certain disadvantages, some of which lead to relatively low yields. Thus, the yield of the reaction in Example 1 of U.S. Pat. No. 4,254,274 and No. 4,365,075—the production of ethyl 2-[4-(2-oxo-1-cyclohexylidenemethyl)phenyl]propionate—was about 32%. The yield of Example 4 of said U.S. Patent—the hydrolysis of this ethyl ester to 2-[4-(2-oxo-1-cyclohexylidenemethyl)phenyl]propionic acid—was 51%. However, the overall yield of the process consisting of Example 1 followed by Example 4 was merely 16.3%, which is undesirably low for a commercial process.

Whilst each of the disadvantages of the prior process is relatively minor, together they can have a significant effect on the economy, and hence profitability and viability, of the process.

We have now discovered how these disadvantages may be overcome in a simple, yet unexpected, way.

BRIEF SUMMARY OF INVENTION

It is, therefore, an object of the present invention to provide a process for preparing cycloalkylidenemethylphenylacetic acid derivatives of formula (I) in a high yield and economically.

In accordance with the present invention, the compounds of formula (I), as defined above, are prepared by reacting, instead of the ester of formula (IIa), the corresponding acid of formula (II):

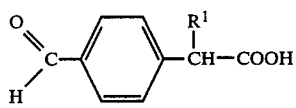

(in which $R^1$ is as defined above) with the aforementioned compound of formula (III) and then hydrolizing the product of this reaction.

DETAILED DESCRIPTION OF INVENTION

From the point of view of their biological activities, we prefer those compounds of formula (I) in which $R^1$ represents a $C_1$–$C_4$ alkyl group and, in particular, those compounds in which n is 1 or 2. Where $R^1$ represents a $C_1$–$C_4$ alkyl group, this may be a straight or branched chain group and examples include the methyl, ethyl, propyl, isopropyl, butyl and isobutyl groups, preferably the methyl group. The most preferred compounds of formula (I) are, therefore, those compounds in which $R^1$ represents a methyl group and n is 1 or 2.

Where $R^1$ represents an alkyl group, the carbon atom to which it is attached is an asymmetric carbon atom. Because of the presence of this asymmetric carbon atom in the resulting compound of formula (I), the compound exists in the form of optical isomers. Although these optical isomers are represented in the above formula (I) by a single structural formula, the present invention contemplates both the individual isolated isomers, as well as mixtures (e.g. racemates) thereof. Where the compound of formula (I) is obtained as a mixture (e.g. a racemate) of optical isomers, these isomers may, if desired, be separated by conventional optical resolution techniques.

The process of the present invention comprises reacting a benzaldehyde derivative of formula (II):

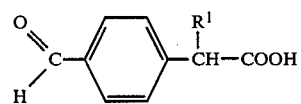

(in which $R^1$ is as defined above) with an enamine derivative of formula (III):

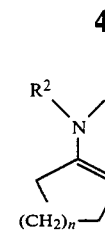

(in which $R^2$, $R^3$ and n are as defined above) and then hydrolizing the product.

The nature of $R^1$ [in the compound of formula (II)] and the value of n [in the compound of formula (III)] are, of course, determined by the nature of the final product which it is desired to achieve and, accordingly, the preferred values for these symbols are as described above in relation to the compounds of formula (I).

In contrast, the groups represented by $R^2$ and $R^3$ are eliminated in the course of the reaction in the process of the invention and these do not affect the nature of the final product. Accordingly, the groups represented by $R^2$ and $R^3$ may be chosen freely, having regard solely to process criteria. Where $R^2$ and $R^3$ represent alkyl groups, these may be straight or branched chain alkyl groups and preferably each has from 1 to 4 carbon atoms. Examples of such groups include the methyl, ethyl, propyl, isopropyl, butyl and isobutyl groups. Alternatively, $R^2$ and $R^3$, together with the nitrogen atom to which they are attached, may represent a nitrogen-containing heterocyclic group, which preferably has from 5 to 10 ring atoms, of which from 1 to 3 [including the nitrogen atom shown in formula (III)] are hetero-atoms selected from the group consisting of nitrogen, oxygen and sulfur atoms, preferably nitrogen and oxygen atoms. More preferably, where $R^2$ and $R^3$ represent such a heterocyclic group, it has 5 or 6 ring atoms and 1 or 2 hetero-atoms [including the nitrogen atom shown in formula (III)] selected from the group consisting of nitrogen and oxygen atoms. Particularly preferred heterocyclic groups which may be represented by $R^2$ and $R^3$ include the 1-pyrrolidinyl, piperidino and morpholino groups.

The first stage in the process of the invention comprises the reaction of the benzaldehyde derivative of formula (II) with the enamine derivative of formula (III). This reaction is normally and preferably carried out in the presence of a solvent. This reaction will take place in a wide range of solvents and, to this extent, the nature of the solvent is not critical, provided that it does not interfere with the reaction. Thus, examples of solvents which can be employed in the present invention include: aromatic hydrocarbons, such as benzene, toluene or xylene; ethers, such as tetrahydrofuran or dioxane; and halogenated aliphatic hydrocarbons, such as chloroform or methylene chloride. However, as described above in relation to the prior art, certain solvents can have environmental disadvantages and/or can necessitate the use of uneconomic reaction conditions, and this applies, in particular, to the aromatic hydrocarbons. It is, therefore, a particular advantage of the process of the present invention, as compared with the prior art process, that it permits the use of such solvents as chlorinated aliphatic hydrocarbons (notably methylene chloride) which, broadly speaking, do not have the same impact on the environment as do the aromatic hydrocarbons. Moreover, as described in more detail below, the use of such chlorinated aliphatic hydrocarbons as the reaction solvent permits the employment of lower reaction temperatures (whilst still completing the reaction within a reasonable time) and hence significantly improves the economy of the process.

The molar ratio of the benzaldehyde of formula (II) to the enamine derivative of formula (III) may vary over a wide range and is not critical to the present invention. However, in general, we prefer to employ a molar excess of the enamine derivative and have found that particularly good results are achieved when the molar ratio of enamine (III) to benzaldehyde (II) is from 1.5:1 to 2.0:1, although good results are also achieved at molar ratios in excess of 2.0:1; however, too much enamine is wasteful as the excess takes no part in the reaction.

The reaction will take place over a wide range of temperatures, for example from 0° to 140° C., more preferably from about ambient temperature to 60° C. In general, temperatures as close to ambient as possible are preferred for industrial processes, in order to minimize energy costs, but this may sometimes be impractical, as higher temperatures, in general, speed chemical reactions and too long a reaction time may be required, unless an elevated temperature is employed. It is a particular advantage of the present invention that chlorinated aliphatic hydrocarbons such as methylene chloride may be used as the reaction solvent, since these permit the reaction to be effected efficiently at a relatively low temperature, e.g. from ambient temperature to 40° C., within a reasonably short period, for example up to 5 or 6 hours. When chloroform is used as the solvent, similar conditions apply, e.g. a reaction temperature from ambient to 50° C. and a period up to about 5 hours.

The time required for the reaction will vary, depending upon many factors, including the reaction temperature and other reaction conditions, notably, as mentioned above, the reaction solvent. In general, a period of from 30 minutes to 30 hours will suffice, although, of course, it is preferred that the reaction conditions should be so chosen as to permit a reaction period towards the lower end of this range.

After completion of the reaction between the enamine (III) and the benzaldehyde (II), the resulting product is subjected to hydrolysis. Although we do not wish to be limited by any theory, it is thought that the condensation product resulting from the reaction of the compounds of formulae (II) and (III) has the formula (IV):

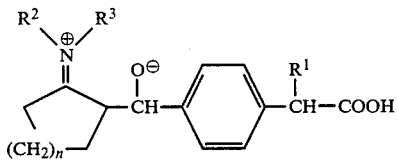

(in which $R^1$, $R^2$, $R^3$ and n are as defined above). The hydrolysis converts this to the desired compound of formula (I) and can be, and preferably is, achieved without intermediate isolation of the intermediate of formula (IV).

This reaction may be carried out by contacting the reaction mixture with a suitable hydrolyzing agent, which may be an acid or a base. The nature of the acid or base employed is not critical and any such compound commonly used in hydrolysis reactions may equally be used in the present invention. However, preferred acids and bases include: mineral acids, such as hydrochloric acid, hydrobromic acid and sulfuric acid; and aqueous solutions of alkali metal hydroxides, such as sodium hydroxide or potassium hydroxide. Of these, the mineral acids are most preferred. There is no particular limitation on the reaction conditions employed but (unlike the ester hydrolysis employed in the prior art) relatively mild conditions may be employed in this hydrolysis reaction. Most conveniently, the reaction is carried out at room temperature. The time required for the reaction will vary, depending primarily upon the reaction temperature and the nature of the hydrolizing agent, but a period of from 10 minutes to 30 hours, more commonly from 30 minutes to 3 hours, will generally suffice, although a shorter or a longer period may also satisfactorily be used, if appropriate.

After completion of the reaction, the desired compound of formula (I) may be recovered from the reaction mixture by conventional means. For example, when a mineral acid is employed as the hydrolizing agent, one suitable recovery technique comprises: extracting the reaction mixture with an organic solvent, such as methylene chloride, diethyl ether or benzene; washing the extract with water and drying it; and finally evaporating off the solvent to give the desired compound. This compound may, if necessary, be further purified by various conventional means, depending upon the physical nature of the products; for example, recrystallization, vacuum distillation (if the product is an oily substance) or the various chromatography techniques, particularly column chromatography.

The invention is further illustrated by the following non-limiting Examples.

EXAMPLE 1

2-[4-(2-Oxocyclohexylidenemethyl)phenyl]propionic acid

A solution of 3.56 g (0.02 mole) of 2-(p-formylphenyl)propionic acid and 10.1 g (0.056 mole) of 1-morpholinocyclohexene in 40 ml of benzene was allowed to stand overnight (12 hours) at room temperature, after which 20 ml of 6N hydrochloric acid were added thereto, and the mixture was stirred for 1 hour at room temperature. The reaction mixture was then extracted with benzene; the extract was washed with water and dried; and the solvent was removed by evaporation under reduced pressure to give a crystalline substance. This was recrystallized from a mixture of diethyl ether and hexane, to give 4.02 g (yield 77.7%) of the title compound as white crystals melting at 108°–110° C.

Elemental analysis: Calculated for $C_{16}H_{18}O_3$: C, 74.39%, H, 7.02%; Found: C, 74.49%, H, 6.86%.

EXAMPLE 2

2-[4-(2-Oxocyclopentylidenemethyl)phenyl]propionic acid

A solution of 3.56 g (0.02 mole) of 2-(p-formylphenyl)propionic acid and 6.4 g (0.04 mole) of 1-morpholinocyclopentene in 40 ml of toluene was stirred at 60° C. for 3 hours. The mixture was cooled, and 20 ml of 6N hydrochloric acid were then added to the cooled solution, after which the mixture was stirred at room temperature for a further 1 hour. The reaction mixture was then extracted with diethyl ether; the extract was washed with water and dried; and the solvent was removed by evaporation under reduced pressure to afford a crystalline substance, which was recrystallized from a mixture of diethyl ether and hexane, to give 4.0 g (yield 82.3%) of the title compound as white crystals melting at 106°–107° C.

Elemental analysis: Calculated for $C_{15}H_{16}O_3$: C, 73.75%, H, 6.60%; Found: C, 74.50%; H, 6.69%.

EXAMPLE 3

4-(2-Oxocyclopentylidenemethyl)phenylacetic acid

A solution of 3.28 g (0.02 mole) of p-formylphenylacetic acid and 5.2 g (0.038 mole) of 1-pyrrolidinocyclopentene (0.038 mole) in 20 ml of benzene was heated under reflux for 1 hour. The solution was then cooled, and 20 ml of 6N hydrochloric acid were added to the cooled solution. The mixture was then stirred for a further 1 hour at room temperature, after which the reaction mixture was extracted with benzene. The extract was washed with water and dried over anhydrous sodium sulfate, and the solvent was removed to give an oily substance, which was distilled under reduced pressure to afford 3.1 g (yield 67.4%) of the title compound as a colorless oily substance boiling at 205°–210° C./0.25 mm Hg (33 Pa).

Elemental analysis: Calculated for $C_{14}H_{14}O_3$: C, 73.02%; H, 6.13%; Found: C, 73.26%; H, 6.13%.

EXAMPLE 4

4-(2-Oxocyclohexylidenemethyl)phenylacetic acid

A solution of 3.28 g (0.02 mole) of p-formylphenylacetic acid and 10.1 g (0.056 mole) of 1-morpholinocyclohexene in 40 ml of benzene was stirred at room temperature for 12 hours, after which 20 ml of 6N hydrochloric acid were added thereto. The mixture was then stirred at room temperature for a further 1 hour, after which it was extracted with diethyl ether. The extract was washed with water and dried over anhydrous sodium sulfate, and the solvent was removed to afford an oily substance, which was purified by silica gel chromatography, eluted with a 1:1 by volume mixture of hexane and ethyl acetate, to give 2.5 g (yield 51.2%) of the title compound as a colorless oily substance.

Elemental analysis: Calculated for $C_{15}H_{16}O_3$: C, 73.75%; H, 6.60%; Found: C, 73.69%, H, 6.61%.

EXAMPLE 5

2-[4-(2-Oxocyclohexylidenemethyl)phenyl]propionic acid 9.71 g (0.055 mole) of 2-(p-formylphenyl)propionic acid and 14.08 g (0.084 mole) of 1-morpholinocyclohexene (a molar ratio of about 1:1.5) were dissolved in 100 ml of methylene chloride, and the resulting solution was heated, with stirring, at 40° C. for 6 hours. At the end of this time, 50 ml of 6N hydrochloric acid were added to the reaction mixture, which was then stirred at room temperature for 1 hour. The mixture was then extracted with methylene chloride and the extract was washed with water and dried. After the solvent had been distilled off under reduced pressure, the resulting crystalline substance was recrystallized from a mixture of ethyl acetate and hexane, to give 11.4 g (yield 81%) of the title compound in the form of white crystals melting at 108°–110° C. The elemental analysis of this product was in substantial agreement with that of the product of Example 1.

EXAMPLE 6

2-[4-(2-Oxocyclohexylidenemethyl)phenyl]propionic acid 9.71 g (0.055 mole) of 2-(p-formylphenyl)propionic acid and 18.77 g (0.11 mole) of 1-morpholinocycloxhexene (a molar ratio of about 1:2) were dissolved in 100 ml of methylene chloride, and the resulting solution was heated, with stirring, at 40° C. for 5 hours. The reaction mixture was then treated as described in Example 5, giving 11.9 g (yield 84.6%) of the title compound. The melting point and elemental analysis of this product were in substantial agreement with those of the product of Example 1.

EXAMPLE 7

2-[4-(2-Oxocyclohexylidenemethyl)phenyl]propionic acid 9.71 g (0.055 mole) of 2-(p-formylphenyl)propionic acid and 18.77 g (0.11 mole) of 1-morpholinocyclohexene (a molar ratio of about 1:2) were dissolved in 100 ml of chloroform, and the resulting mixture was heated, with stirring, at 50° C. for 3 hours. The reaction mixture was then treated as described in Example 5, to give 10.1 g (yield 71.8%) of the title compound. The melting point and elemental analysis of this product were in substantial agreement with those of the product of Example 1.

We claim:

1. A process for preparing a compound of formula (I):

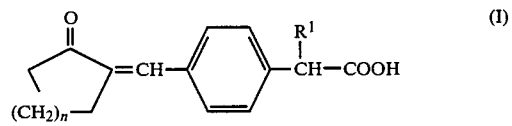

wherein $R^1$ represents a hydrogen atom or a $C_1$–$C_4$ alkyl group and n is an integer of from 1 to 3, which process comprises reacting a benzaldehyde acid compound of formula (II):

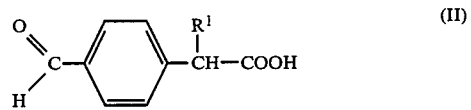

in which $R^1$ is as defined above with an enamine derivative of formula (III):

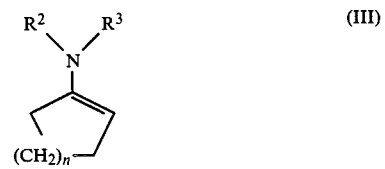

in which:

n is as defined above; and $R^2$ and $R^3$ are independently selected from the group consisting of $C_1$–$C_6$ alkyl groups, or $R^2$ and $R^3$, together with the nitrogen atom to which they are attached, represent a cyclic amino group, of which the remaining ring atoms are selected from the group consisting of carbon, nitrogen, oxygen and sulfur atoms, and then hydrolizing the product of this reaction to give said compound of formula (I).

2. A process as claimed in claim 1, wherein $R^1$ represents a $C_1-C_4$ alkyl group.

3. A process as claimed in claim 2, wherein $R^1$ represents a methyl group.

4. A process as claimed in claim 1, wherein n is 1 or 2.

5. A process as claimed in claim 1, wherein $R^1$ represents a $C_1-C_4$ alkyl group and n is 1 or 2.

6. A process as claimed in claim 1, wherein $R^1$ represents a methyl group and n is 1 or 2.

7. A process as claimed in claim 1, wherein $R^2$ and $R^3$, together with the nitrogen atom to which they are attached, represent a nitrogen-containing heterocyclic group having from 5 to 10 ring atoms of which from 1 to 3, including the nitrogen atom shown in formula (III), are hetero-atoms selected from the group consisting of nitrogen, oxygen and sulfur atoms.

8. A process as claimed in claim 7, wherein said hetero-atoms are selected from the group consisting of nitrogen and oxygen atoms.

9. A process as claimed in claim 7, wherein said heterocyclic group has 5 or 6 ring atoms and 1 or 2 heteroatoms, including the nitrogen atom shown in formula (III), selected from the group consisting of nitrogen and oxygen atoms.

10. A process as claimed in claim 7, wherein $R^2$ and $R^3$, together with the nitrogen atom to which they are attached, represent a 1-pyrrolidinyl, piperidino or morpholino group.

11. A process as claimed in claim 1, wherein the reaction between said benzaldehyde acid (II) and said enamine derivative (III) is effected in the presence of a solvent selected from the group consisting of aromatic hydrocarbons, ethers and halogenated aliphatic hydrocarbons.

12. A process as claimed in claim 11, wherein said solvent is at least one solvent selected from the group consisting of benzene, toluene and xylene.

13. A process as claimed in claim 11, wherein said solvent is at least one solvent selected from the group consisting of chloroform and methylene chloride.

14. A process as claimed in claim 11, wherein said solvent is methylene chloride.

15. A process as claimed in claim 1, wherein the molar ratio of said enamine (III) to said benzaldehyde acid (II) is from 1.5:1 to 2.0:1.

16. A process as claimed in claim 1, wherein the molar ratio of said enamine (III) to said benzaldehyde acid (II) is at least 2.0:1.

17. A process as claimed in claim 1, wherein the reaction between said benzaldehyde acid (II) and said enamine (III) is effected at a temperature of from 0° to 140° C.

18. A process as claimed in claim 17, wherein said reaction is effected at a temperature of from ambient temperature to 60° C.

19. A process as claimed in claim 11, wherein said reaction is effected at the reflux temperature of the solvent employed.

20. A process as claimed in claim 14, wherein said reaction is effected at a temperature from ambient temperature to 40° C.

21. A process as claimed in claim 1, wherein the hydrolysis is effected by means of a hydrolizing agent selected from the group consisting of mineral acids and aqueous solutions of alkali metal hydroxides.

22. A process as claimed in claim 21, wherein said hydrolizing agent is a mineral acid selected from the group consisting of hydrochloric acid, hydrobromic acid and sulfuric acid.

23. A process as claimed in claim 22, wherein said mineral acid is hydrochloric acid.

24. A process as claimed in claim 1, wherein said hydrolysis is effected at about ambient temperature.

25. A process for preparing a compound of formula (I):

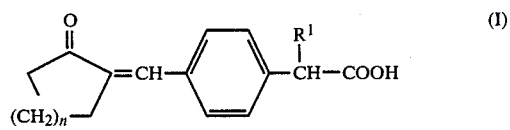

wherein:

$R^1$ represents a $C_1-C_4$ alkyl group and n is 1 or 2 which process comprises reacting a benzaldehyde acid compound of formula (II):

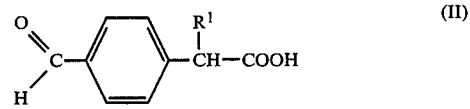

in which $R^1$ is as defined above with an enamine derivative of formula (III):

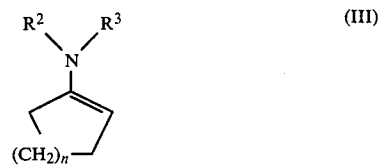

in which:

n is as defined above; and $R^2$ and $R^3$ are independently selected from the group consisting of $C_1-C_6$ alkyl groups, or $R^2$ and $R^3$, together with the nitrogen atom to which they are attached, represent a nitrogen-containing heterocyclic group having from 5 to 10 ring atoms of which from 1 to 3, including the nitrogen atom shown in formula (III), are hetero-atoms selected from the group consisting of nitrogen, oxygen and sulfur atoms, and then hydrolizing the product of this reaction to give said compound of formula (I).

26. A process as claimed in claim 25, wherein $R^1$ represents a methyl group.

27. A process as claimed in claim 25, wherein said hetero-atoms are selected from the group consisting of nitrogen and oxygen atoms.

28. A process as claimed in claim 25, wherein $R^2$ and $R^3$, together with the nitrogen atom to which they are attached, represent a 1-pyrrolidinyl, piperidino or morpholino group.

29. A process as claimed in claim 25, wherein the reaction between said benzaldehyde acid (II) and said enamine derivative (III) is effected in the presence of a solvent selected from the group consisting of aromatic hydrocarbons, ethers and halogenated aliphatic hydrocarbons.

30. A process as claimed in claim 29, wherein said solvent is at least one solvent selected from the group consisting of benzene, toluene and xylene.

31. A process as claimed in claim 29, wherein said solvent is at least one solvent selected from the group consisting of chloroform and methylene chloride.

32. A process as claimed in claim 29, wherein said solvent is methylene chloride.

33. A process as claimed in claim 25, wherein the molar ratio of said enamine (III) to said benzaldehyde acid (II) is from 1.5:1 to 2.0:1.

34. A process as claimed in claim 25, wherein the molar ratio of said enamine (III) to said benzaldehyde acid (II) is at least 2.0:1.

35. A process for preparing a compound of formula (I):

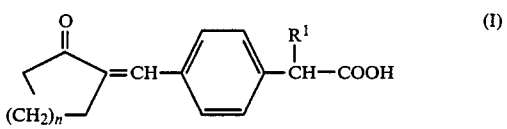

wherein:
R$^1$ represents a hydrogen atom or a C$_1$–C$_4$ alkyl group; and
n is an integer of from 1 to 3
which process comprises reacting a benzaldehyde acid compound of formula (II):

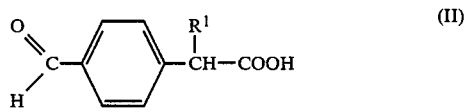

in which R$^1$ is as defined above with an enamine derivative of formula (III):

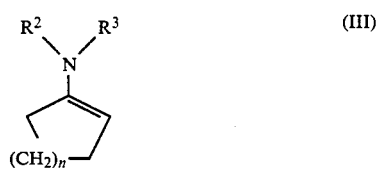

in which:

n is as defined above; and
R$^2$ and R$^3$ are independently selected from the group consisting of C$_1$–C$_6$ alkyl groups, or R$^2$ and R$^3$, together with the nitrogen atom to which they are attached, represent a cyclic amino group, of which the remaining ring atoms are selected from the group consisting of carbon, nitrogen, oxygen and sulfur atoms in the presence of a solvent selected from the group consisting of halogenated aliphatic hydrocarbons and at a temperature from ambient temperature to the reflux temperature of said solvent, and then hydrolizing the product of this reaction to give said compound of formula (I).

36. A process as claimed in claim 35, wherein R$^1$ represents a C$_1$–C$_4$ alkyl group and n is 1 or 2.

37. A process as claimed in claim 36, wherein R$^1$ represents a methyl group and n is 1 or 2.

38. A process as claimed in claim 35, wherein R$^2$ and R$^3$, together with the nitrogen atom to which they are attached, represent a nitrogen-containing heterocyclic group having from 5 to 10 ring atoms of which from 1 to 3, including the nitrogen atom shown in formula (III), are hetero-atoms selected from the group consisting of nitrogen, oxygen and sulfur atoms.

39. A process as claimed in claim 38, wherein said hetero-atoms are selected from the group consisting of nitrogen and oxygen atoms.

40. A process as claimed in claim 38, wherein said heterocyclic group has 5 or 6 ring atoms and 1 or 2 hetero-atoms, including the nitrogen atom shown in formula (III), selected from the group consisting of nitrogen and oxygen atoms.

41. A process as claimed in claim 38, wherein R$^2$ and R$^3$, together with the nitrogen atom to which they are attached, represent a 1-pyrrolidinyl, piperidino or morpholino group.

42. A process as claimed in claim 35, wherein said solvent is at least one solvent selected from the group consisting of chloroform and methylene chloride.

43. A process as claimed in claim 35, wherein said solvent is methylene chloride.

44. A process as claimed in claim 35, wherein the molar ratio of said enamine (III) to said benzaldehyde acid (II) is from 1.5:1 to 2.0:1.

45. A process as claimed in claim 43, wherein said reaction is effected at a temperature from ambient temperature to 40° C.

* * * * *